(12) United States Patent
Park

(10) Patent No.: US 12,104,990 B2
(45) Date of Patent: Oct. 1, 2024

(54) APPARATUS FOR COLLECTING AND STORING FLUID SAMPLES FROM VEHICLES AND MACHINERY

(71) Applicant: Shane Park, Greenfields (AU)

(72) Inventor: Shane Park, Greenfields (AU)

(73) Assignee: Shane Park, Greenfields (AU)

( * ) Notice: Subject to any disclaimer, the term of this patent is extended or adjusted under 35 U.S.C. 154(b) by 274 days.

(21) Appl. No.: 17/783,876

(22) PCT Filed: Dec. 15, 2020

(86) PCT No.: PCT/AU2020/000136
§ 371 (c)(1),
(2) Date: Jun. 9, 2022

(87) PCT Pub. No.: WO2021/119719
PCT Pub. Date: Jun. 24, 2021

(65) Prior Publication Data
US 2023/0014467 A1    Jan. 19, 2023

(30) Foreign Application Priority Data

Dec. 16, 2019 (AU) .............................. 2019904738
Sep. 18, 2020 (AU) .............................. 2020903351

(51) Int. Cl.
*G01N 1/14* (2006.01)
*B65D 41/04* (2006.01)
(Continued)

(52) U.S. Cl.
CPC .............. *G01N 1/14* (2013.01); *B65D 41/04* (2013.01); *B65D 41/20* (2013.01);
(Continued)

(58) Field of Classification Search
None
See application file for complete search history.

(56) References Cited

U.S. PATENT DOCUMENTS 3,010,583 A    11/1961 Kenyon
4,251,366 A    2/1981 Simon et al.
(Continued)

FOREIGN PATENT DOCUMENTS

EP        1 011 604 B1    9/2004
KR     2010-0030914 A    3/2010
(Continued)

OTHER PUBLICATIONS

Scheduled Oil Sampling Using a Vacuum Pump [Viewed on Feb. 10, 2021]. Viewed on internet. <URL:https://www.youtube.com/watch?v=OAJ1rZsrqJU>, Published on Jun. 5, 2009, 0:56-1:05 & 1:12-1:21 Cited in the PCT/ISA/210 of PCT/AU2020/000136.

*Primary Examiner* — Patrick Assouad
*Assistant Examiner* — Mark A Shabman
(74) *Attorney, Agent, or Firm* — Carrier, Shende & Associates P.C.; Joseph P. Carrier; Fulchand P. Shende

(57) ABSTRACT

An apparatus for collecting and storing fluid samples from vehicles and machinery comprises a storage container having a fluid inlet sealed by a cap, the cap having an aperture releasably sealed by a lid. An adapter connects the cap releasably to a fluid outlet coupling port of a fluid sampling device. The adapter comprises a lumen, having an inlet and an outlet aperture, an external screw thread engageable with an internal screw thread of the coupling port and a connector assembly for connecting the adapter releasably to the cap. A penetrable diaphragm provides an airtight seal over a storage region of the storage container. When the adapter is connected to the coupling port and the cap is connected to the adapter, a fluid outlet tube extending from the coupling port extends through the aperture and protrudes through one or more perforations provided in the penetrable diaphragm into the storage region.

18 Claims, 18 Drawing Sheets

(51) Int. Cl.
  *B65D 41/20* (2006.01)
  *B65D 47/08* (2006.01)
  *B65D 51/00* (2006.01)
  *B67C 11/00* (2006.01)
  *B67C 11/02* (2006.01)
  *G01N 33/28* (2006.01)

(52) U.S. Cl.
  CPC ....... *B65D 47/0814* (2013.01); *B65D 51/002* (2013.01); *B67C 11/02* (2013.01); *G01N 33/28* (2013.01); *B67C 2011/022* (2013.01); *B67C 2011/20* (2013.01); *G01N 2001/1418* (2013.01)

(56) References Cited

U.S. PATENT DOCUMENTS

| | | | |
|---|---|---|---|
| 4,301,010 A | 11/1981 | Eddleman et al. | |
| 6,168,037 B1* | 1/2001 | Grimard | A61J 1/2096 |
| | | | 215/310 |
| 8,303,914 B2* | 11/2012 | Zurcher | B01L 3/50825 |
| | | | 422/549 |
| 2004/0100415 A1* | 5/2004 | Veitch | G06K 19/07758 |
| | | | 343/850 |
| 2006/0071000 A1 | 4/2006 | Weist et al. | |
| 2014/0011292 A1 | 1/2014 | Lentz et al. | |
| 2014/0053662 A9* | 2/2014 | Kacian | B65D 51/002 |
| | | | 422/534 |
| 2016/0184182 A1* | 6/2016 | Gross | B65D 51/18 |
| | | | 215/316 |
| 2017/0042460 A1 | 2/2017 | Holmes et al. | |
| 2018/0297752 A1* | 10/2018 | Mai | B65D 51/1688 |
| 2019/0046406 A1* | 2/2019 | McDowell | A61J 1/14 |
| 2019/0105484 A1 | 4/2019 | Doornbos et al. | |

FOREIGN PATENT DOCUMENTS

| | | |
|---|---|---|
| WO | 2007/003283 A1 | 1/2007 |
| WO | 2015/100169 A1 | 7/2015 |
| WO | 2018/169877 A1 | 9/2018 |

\* cited by examiner

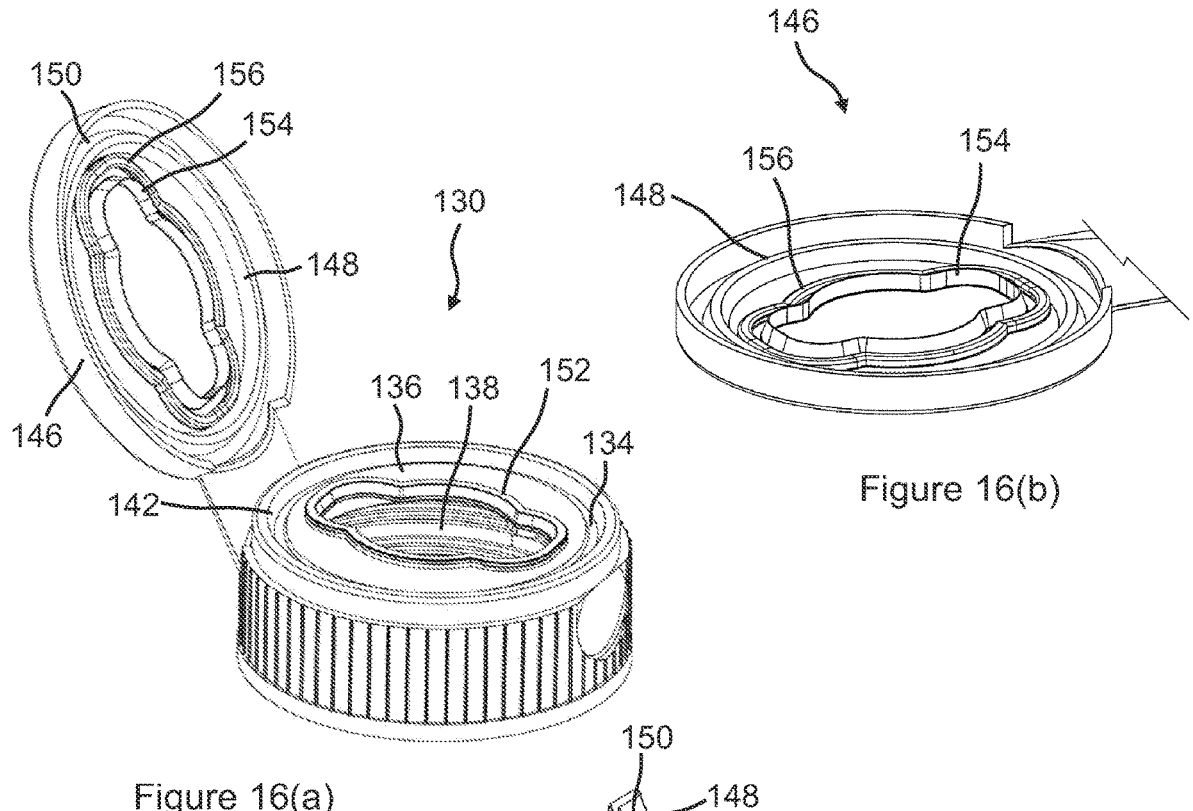
Figure 16(b)
Figure 16(a)
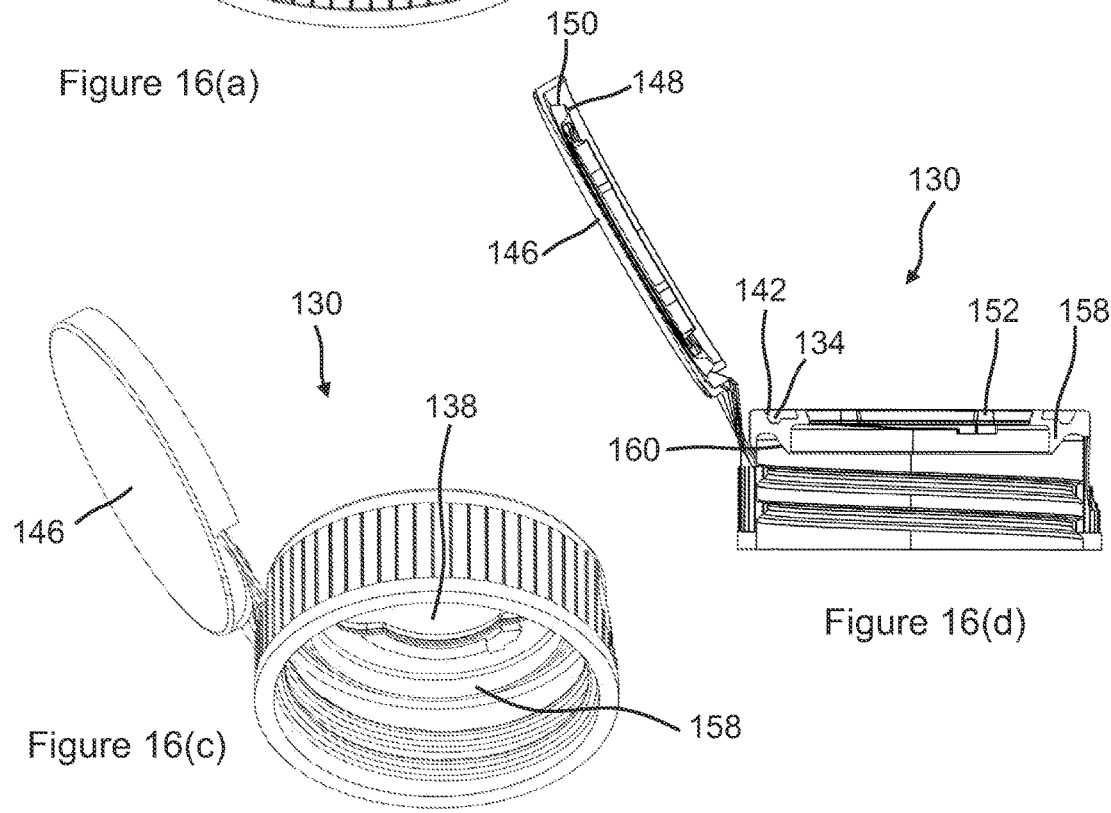
Figure 16(d)
Figure 16(c)

APPARATUS FOR COLLECTING AND STORING FLUID SAMPLES FROM VEHICLES AND MACHINERY

FIELD

The present invention relates to fluid sampling apparatus and, more particularly, to an apparatus for collecting and storing fluid samples from vehicles and machinery.

BACKGROUND

Fluid samples often need to be taken from vehicles and machines. For example, oil and brake fluid samples are periodically taken from component compartments in excavators and other heavy duty vehicles used in mining and construction. Fluid samples are taken for a variety of reasons pertaining to vehicle maintenance and safety. Internal vehicle parts and machinery gradually wear over time which can lead to traces of metal finding their way into compartment fluids. Fluid samples are, therefore, taken and analysed in a laboratory to assess the condition of such components and to predict future wear. Vehicles and machinery are commonly provided with outlets that allow fluid samples to be taken. For example, an excavator typically has one or more sealable outlets that are fluidly connected to engine compartments containing oil. The outlets are typically located on the outside of the vehicle near to the relevant compartments. Some larger vehicles feature a permanently mounted remote sampling station that serves to move the engine component sample point(s) to an area of greater convenience.

To extract an oil sample, a fluid sampling device may be connected to the relevant outlet or sampling station of the vehicle. For example, a handheld vacuum pump is commonly used as a fluid sampling device. To connect the pump, a sampling tube of the pump is attached to the relevant collection point and a bottle, or similar storage container, is then connected to the pump. To connect the bottle to the pump, the pump normally includes an outlet coupling port that has an internal screw thread that receives and engages with an external screw thread on the bottle's neck. The sampling tube includes an outlet tube section that downwardly extends out of the outlet coupling port. The outlet tube section protrudes into the bottle when the bottle is connected to the coupling port. The pump is operated by hand causing oil to be sucked from the relevant vehicle compartment into the bottle until a required quantity has been collected.

This collection procedure is problematic because unwanted particulates, fluids and gases can contaminate the oil and/or bottle when the sample is being taken. This happens, in particular, when the open mouth of the bottle is exposed to the environment when being received by the pump's coupling port. Contamination leads to incorrect test results in the laboratory and erroneous diagnosis of vehicle component conditions. In an effort to avoid contamination, the bottle, which is typically supplied at a known cleanliness, is stored initially inside a sealed plastic bag. To retrieve the fluid sample, the cap of the bagged bottle is firstly removed by gripping and twisting the cap through the bag. The bottle is then connected to the pump's coupling port by pushing the bottle's open mouth into the coupling port through the bag. During this process, the pump's downwardly extending fluid outlet tube punctures through a part of the bag that covers the bottle's mouth so that an outlet end of the tube protrudes into the bottle. The bottle is then twisted causing its neck to screw into the internal screw thread of the pump's coupling port.

The fluid sample is then extracted using the vacuum pump. Once collected, the bottle is gripped through the bag and unscrewed from the pump. With the bottle free and still inside of the bag, the bottle's cap is then retrieved from the bottom of the bag, arranged onto the bottle's mouth and tightened. Once the bottle is safely capped, the bag is opened and the bottle is removed. Whilst this method enables some contamination to be avoided, it is difficult to perform and is not foolproof. Unwanted substances and materials may still come into contact with the fluid sample when flowing into the bottle, particularly when the method is performed in hot, dusty and windy environments.

References to prior art documents in this specification are provided for illustrative purposes only and are not to be taken as an admission that such prior art is part of the common general knowledge in Australia or elsewhere.

SUMMARY

According to the present invention, there is provided an apparatus for collecting and storing fluid samples from vehicles and machinery, the apparatus comprising:
(a) a storage container having a fluid inlet;
(b) a cap for sealing the fluid inlet, wherein the cap comprises an aperture provided in a surface of the cap and a lid for releasably sealing the aperture;
(c) an adapter for connecting the cap releasably to a fluid outlet coupling port of a fluid sampling device, the fluid sampling device being adapted to collect a fluid sample from a vehicle or machine, wherein the adapter comprises:
 a cylindrical body having an internal lumen extending longitudinally through the cylindrical body with an inlet aperture and an outlet aperture disposed at, respectively, uppermost and lowermost ends of the cylindrical body;
 an external screw thread extending around an outermost surface of the cylindrical body, wherein the external screw thread is adapted to engage threadedly with an internal screw thread extending around an innermost cylindrical surface of an aperture of the fluid outlet coupling port;
 a connector assembly for connecting the adapter releasably to the cap such that the outlet aperture of the cylindrical body is fluidly aligned with the aperture of the cap, wherein the surface of the cap and the lowermost end of the cylindrical body are mutually adapted to provide an airtight seal therebetween when the adapter and cap are connected together by the connector assembly;
(d) a penetrable diaphragm that is connected to an inside surface of either the cap or the storage container to provide an airtight seal over a storage region of the storage container below the penetrable diaphragm, wherein one or more perforations are provided in a surface of the penetrable diaphragm,
wherein the cap and adapter are mutually dimensioned such that a fluid outlet tube extending out from the fluid outlet coupling port extends through the aperture of the cap and protrudes through the perforations into the storage region when the adapter is connected to the fluid outlet coupling port and the cap is connected to the adapter by the connector assembly.

The apparatus may also comprise a funnel comprising a fluid outlet tube, wherein the funnel is removably insertable into the cylindrical body of the adapter such that the fluid outlet tube of the funnel is in fluid communication with a fluid outlet of the fluid outlet coupling port. In such example, the cap and adapter are mutually dimensioned such that the fluid outlet tube of the funnel extends through the aperture of the cap and protrudes through the perforations into the storage region when the adapter is connected to the fluid outlet coupling port and the cap is connected to the adapter by the connector assembly.

The connector assembly may comprise a twist lock mechanism.

The twist lock mechanism may comprise a boss downwardly extending from the cylindrical body, the boss comprising one or more outwardly protruding locking members that engage an underside of the cap when the cap and adapter are twisted relative to each other.

One or more lugs may be provided on the underside of the cap, wherein the locking members bear against the lugs when the cap and adapter are twisted relative to each other by a maximum extent.

An annular channel may be provided in the surface of the cap that extends around the aperture of the cap, and an annular ridge may protrude downwardly from the lowermost of the ends of the cylindrical body that is adapted to engage into the annular channel when the adapter and cap are connected together.

A radially outermost wall of the annular channel and a radially outermost wall of the annular ridge may be mutually tapered such that they engage each other diagonally relative to the surface of the cap.

The lid may comprise an annular ridge that protrudes downwardly from an underside of the lid that is adapted to engage into the annular channel when the lid is closed.

The radially outermost wall of the annular channel and a radially outermost wall of the annular ridge of the lid may be mutually tapered such that they engage each other diagonally relative to the surface of the cap.

One or more perforations may provide that a plurality of elastically bendable flaps cover an entry region of the penetrable diaphragm that receives the fluid outlet tube.

The cap may comprise a screw thread that threadedly engages with a complimentary screw thread provided on the fluid inlet of the storage container.

The cap may comprise an annular projection extending downwardly from an underside of the cap, and a radially outermost surface of the annular projection may be tapered and adapted to bear against an annular lip of the fluid inlet of the storage container when the cap is attached thereto.

The lid may comprise a skirt protruding downwardly from an underside of the lid, wherein the skirt is dimensioned to bear against an innermost wall of the aperture of the cap when the lid seals the aperture.

The skirt and innermost wall of the aperture may be mutually tapered to engage each other diagonally relative to the surface of the cap when the lid seals the aperture of the cap.

The cap may comprise a peripheral ridge that upwardly extends from the surface of the cap around a perimeter of the aperture of the cap, and the lid may comprise a second skirt protruding downwardly from an underside of the lid, wherein the second skirt is dimensioned to engage with a radially outermost wall of the peripheral ridge when the lid seals the aperture of the cap.

The apparatus may comprise at least one air vent to allow air to escape from the storage container when fluid flows therein from the fluid sampling device.

The apparatus may comprise a digital storage device for recording data relating to a fluid sample contained in the storage container.

The digital storage device may be provided with a wireless transceiver for transferring and receiving data relating to the fluid sample to and from a peripheral device remote from the storage container.

The digital storage device may comprise an RFID.

The digital storage device may be attached to or embedded in a sticker or label affixed to a side of the storage container.

The present invention also provides an apparatus for collecting and storing fluid samples from vehicles and machinery, the apparatus comprising:
  (a) a storage container having a fluid inlet;
  (b) a cap for sealing the fluid inlet, wherein the cap comprises an aperture provided in a surface of the cap and a lid for releasably sealing the aperture;
  (c) an adapter for connecting the cap releasably to a fluid outlet coupling port of a fluid sampling device, the fluid sampling device being adapted to collect a fluid sample from a vehicle or machine, wherein the adapter comprises:
    a cylindrical body having an internal lumen extending longitudinally through the cylindrical body with an inlet aperture and an outlet aperture disposed at, respectively, uppermost and lowermost ends of the cylindrical body;
    an external screw thread extending around an outermost surface of the cylindrical body, wherein the external screw thread is adapted to engage threadedly with an internal screw thread extending around an innermost cylindrical surface of an aperture of the fluid outlet coupling port;
    a connector assembly for connecting the adapter releasably to the cap such that the outlet aperture of the cylindrical body is fluidly aligned with the aperture of the cap, wherein the surface of the cap and the lowermost end of the cylindrical body are mutually adapted to provide an airtight seal therebetween when the adapter and cap are connected together by the connector assembly;
  (d) a penetrable diaphragm that is connected to an inside surface of either the cap or the storage container to provide an airtight seal over a storage region of the storage container below the penetrable diaphragm, wherein one or more perforations are provided in a surface of the penetrable diaphragm; and
  (e) a funnel comprising a fluid outlet tube, wherein the funnel is removably insertable into the cylindrical body of the adapter such that the fluid outlet tube of the funnel is in fluid communication with a fluid outlet of the fluid outlet coupling port, wherein the cap and adapter are mutually dimensioned such that the fluid outlet tube of the funnel extends through the aperture of the cap and protrudes through the perforations into the storage region when the adapter is connected to the fluid outlet coupling port and the cap is connected to the adapter by the connector assembly.

The present invention also provides an apparatus for collecting and storing fluid samples from vehicles and machinery, the apparatus comprising:
  (a) a storage container having a fluid inlet;
  (b) a cap for sealing the fluid inlet, wherein the cap comprises an aperture provided in a surface of the cap and a lid for releasably sealing the aperture;

(c) an adapter for connecting the cap releasably to a fluid outlet coupling port of a fluid sampling device, the fluid sampling device being adapted to collect a fluid sample from a vehicle or machine, wherein the adapter comprises:
- a cylindrical body having an internal lumen extending longitudinally through the cylindrical body with an inlet aperture and an outlet aperture disposed at, respectively, uppermost and lowermost ends of the cylindrical body;
- a fastener for fastening the cylindrical body releasably to the fluid outlet coupling port;
- a connector assembly comprising a twist lock mechanism for connecting the adapter releasably to the cap such that the outlet aperture of the cylindrical body is fluidly aligned with the aperture of the cap, wherein the surface of the cap and the lowermost end of the cylindrical body are mutually adapted to provide an airtight seal therebetween when the adapter and cap are connected together by the connector assembly;

(d) a penetrable diaphragm that is connected to an inside surface of either the cap or the storage container to provide an airtight seal over a storage region of the storage container below the penetrable diaphragm, wherein one or more perforations are provided in a surface of the penetrable diaphragm, wherein the cap and adapter are mutually dimensioned such that a fluid outlet tube extending out from the fluid outlet coupling port, or a fluid outlet tube of a funnel placed inside the cylindrical body in fluid communication with a fluid outlet of the fluid outlet coupling port, extends through the aperture of the cap and protrudes through the perforations into the storage region when the adapter is connected to the fluid outlet coupling port and the cap is connected to the adapter by the connector assembly.

BRIEF DESCRIPTION OF DRAWINGS

Embodiments of the invention will now be described by way of example only with reference to the accompanying drawings, in which:

FIG. 16(a) is an isometric view of a cap included in an apparatus for collecting and storing fluid samples from vehicles and machinery according to a further example embodiment of the invention;

FIG. 16(b) is an isometric view of a lid of the cap of FIG. 16(a);

FIG. 16(c) is an isometric view of the cap of FIG. 16(a) from an underside of the cap;

FIG. 16(d) is a cross sectional side elevation view of the cap of FIG. 16(a);

DESCRIPTION OF EMBODIMENTS

Figure 1A:
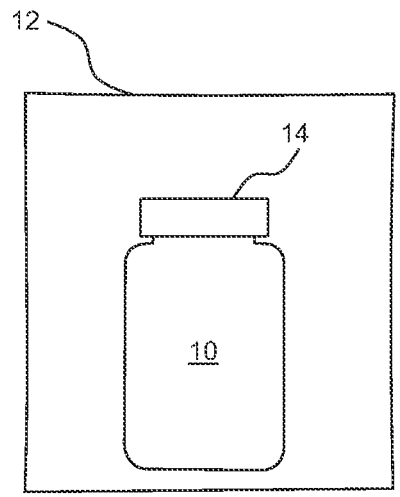
FIGS. 1(a) to 1(c) show a set of components used in a known method for collecting fluid samples from vehicles and machinery.
Figure 1B:
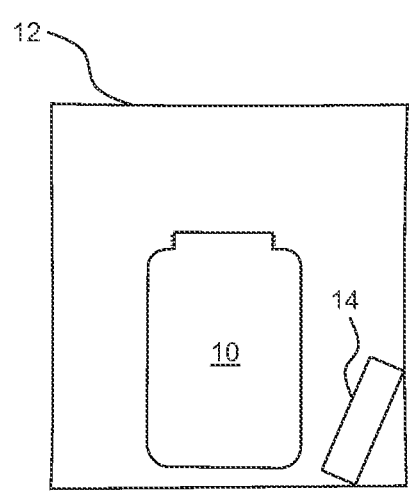
Figure 1C:
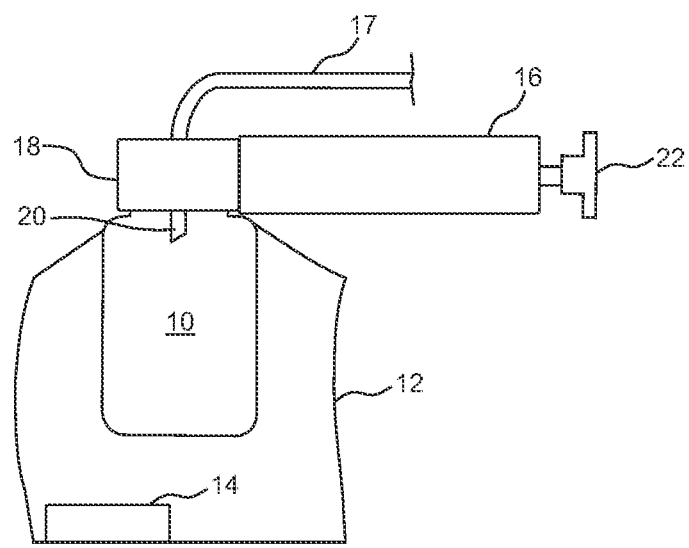

FIGS. 1(a) to 1(c) show a set of components used in a known method for collecting fluid samples from vehicles and machinery. The method is used in a range of situations including, for example, when obtaining oil or brake fluid samples from heavy duty vehicles and machinery used in construction and mining.

FIG. 1(a) shows a sterilised sample bottle 10 that is stored inside a plastic bag 12. The bag 12 is sealed and protects the bottle 10 from contamination during storage and transit. The bag 12 may have a resealable strip at one end (not shown) that enables the bottle 10 to be removed from the bag 12. To avoid contamination, when the fluid sample is being taken the bag 12 is not opened and the bottle 10 is kept inside of the bag 12. To retrieve the sample, the cap 14 of the bottle 10 is firstly removed from the bottle 10 by gripping and twisting the cap 14 through the bag 12. As shown in FIG. 1(b), the cap 14 falls to the bottom of the bag 12 once removed.

As shown in FIG. 1(c), the bagged bottle 10 is then connected to a fluid sampling device 16. In the example depicted, the fluid sampling device 16 comprises a handheld vacuum pump of the type that is commonly used to extract oil samples from earth moving machines and other large construction vehicles. The pump 16 includes a sampling tube 17 that is connected fluidly to the relevant vehicle compartment or sampling station that a fluid sample is to be taken from. The pump 16 comprises a fluid outlet coupling port 18 that is used to connect the pump 16 to bottles and similar storage apparatus. An internally threaded aperture is provided in an underside of the coupling port 18. To establish the connection with the bagged bottle 10, the neck of the bottle 10 is arranged underneath the coupling port 18 and is pushed into the threaded aperture of the port 18 through the bag 12. During this process, the fluid outlet tube 20 of the vacuum pump 16 punctures through the part of the bag 12 covering the bottle's mouth causing the outlet end of the tube 20 to protrude downwards into the bottle 10. The bottle 10 and vacuum pump 16 are then twisted relative to one another which causes the screw thread on the outside of the neck of the bottle 10 to screw into the internal screw thread in the coupling port 18.

The fluid sample is then taken by pumping the handle 22 of the vacuum pump 16 until the required amount of fluid has collected in the bottle 10. The bottle 10 is then gripped through the bag 12 and unscrewed from the coupling port 18. With the bottle 10 free and still inside the bag 12, the cap 14 is retrieved from the bottom of the bag 12 and arranged onto the mouth of the bottle 10 and tightened. With the bottle 10 safely capped, the bag 12 may then be opened and the capped bottle 10 removed. While this method enables some contamination to be avoided when the fluid sample is being taken, the method is not foolproof and some unwanted particulates, gases and liquids can still come into contact with the sample when entering the bottle 10. Contamination is still possible, in particular, when the vacuum pump 16 has been removed from the bagged bottle 10 and the cap 14 is being put back on the bottle 10. The method is impractical, time consuming and tricky to perform, particularly in hot, dusty and windy environments.

Referring to FIGS. 2 to 15, an example embodiment of the present invention provides an apparatus 30 for collecting and storing fluid samples from vehicles and machinery. The apparatus 30 comprises a storage container 32 having a fluid inlet 34 and a cap 36 for sealing the fluid inlet 34. The cap 36 comprises an aperture 38 provided in a surface 39 of the cap 36 and a lid 40 for releasably sealing the aperture 38. The apparatus 30 also comprises an adapter 42 for connecting the cap 36 releasably to a fluid outlet coupling port 44 of a fluid sampling device 46, e.g. FIG. 15(b), wherein the fluid sampling device 46 is adapted to collect a fluid sample from a vehicle or machine 48. The adapter 42 comprises a cylindrical body 50 having an internal lumen 52 extending longitudinally through the body 50 with an inlet aperture 54 and an outlet aperture 56 disposed at, respectively, uppermost and lowermost ends of the body 50.

The adapter 42 also comprises an external screw thread 58 extending around an outermost surface of the cylindrical body 50, wherein the external screw thread 58 is adapted to engage threadedly with an internal screw thread 60 extending around an innermost cylindrical surface of an aperture 62 of the fluid outlet coupling port 44. The adapter 42 also comprises a connector assembly 64 for connecting the adapter 42 releasably to the cap 36 such that the outlet aperture 56 of the cylindrical body 50 is fluidly aligned with the aperture 38 of the cap 36. The surface 39 of the cap 36 and the lowermost circular end of the cylindrical body 50 are mutually adapted to provide an airtight seal therebetween when the adapter 42 and cap 36 are connected together by the connector assembly 64. The apparatus 30 also comprises a penetrable diaphragm 66 that is connected to an inside surface of either the cap 36 or the storage container 32 to provide an airtight seal over a storage region 68 of the storage container 32, wherein the storage region 68 is below the penetrable diaphragm 66. One or more perforations 70 are provided in a surface of the penetrable diaphragm 66.

Figures 15A, 15B, 15C, 15D:
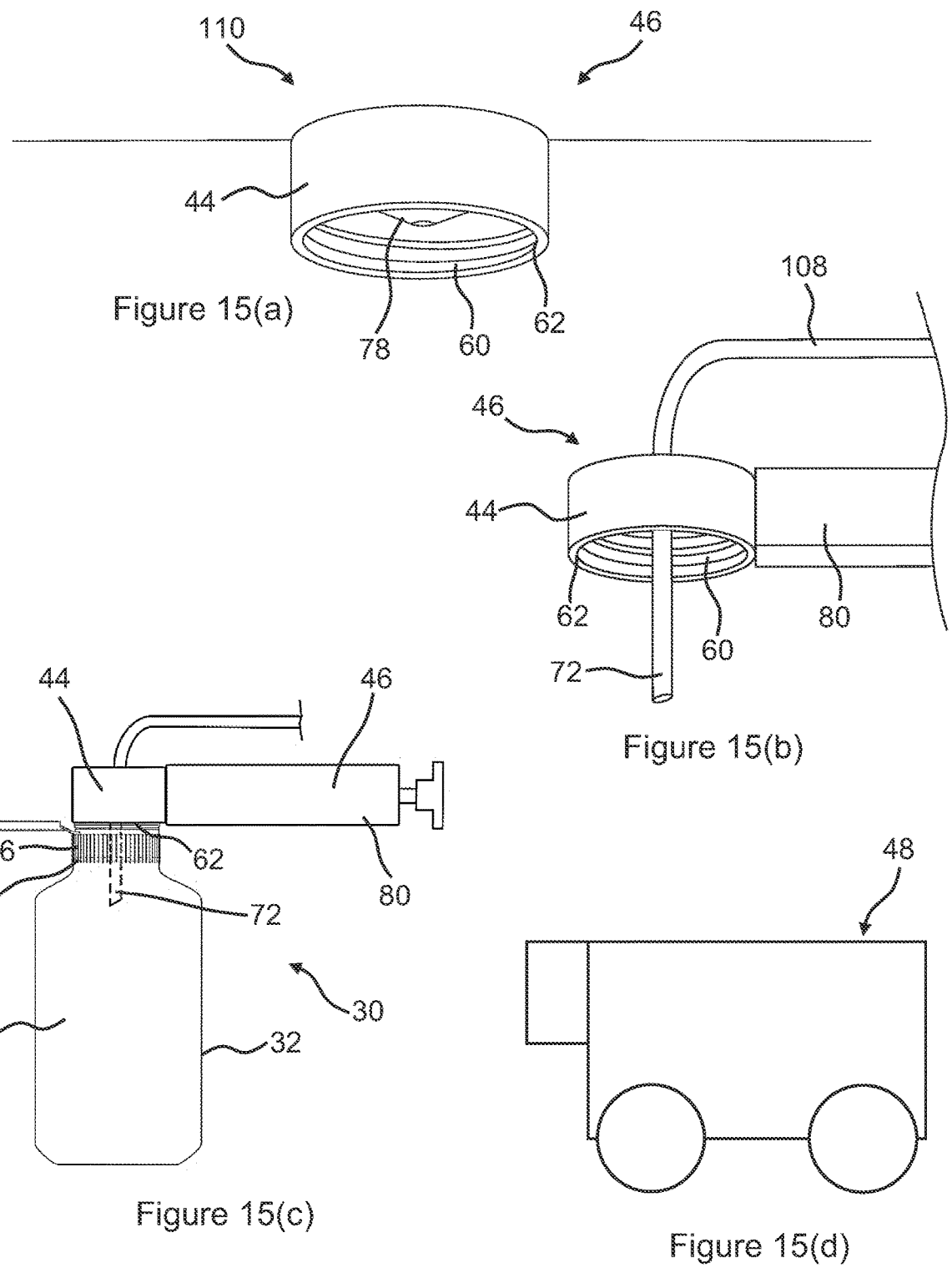
FIG. 15(a) is a schematic view of a fluid outlet coupling port of an integrated fluid sampling device provided on a vehicle.
FIG. 15(b) is an enlarged isometric view of a fluid outlet coupling port of a handheld vacuum pump fluid sampling device.
FIG. 15(c) is a side elevation view of the apparatus connected to the handheld vacuum pump.
FIG. 15(d) is a schematic side elevation view of a mining vehicle.

Referring to FIG. 15(c), the cap 36 and adapter 42 are mutually dimensioned such that a fluid outlet tube 72 extending out from the fluid outlet coupling port 44 of the fluid sampling device 46 extends through the aperture 38 of the cap 36 and protrudes through the perforations 70 of the penetrable diaphragm 66 into the storage region 68 when the adapter 42 is connected to the fluid outlet coupling port 44 and the cap 36 is connected to the adapter 42 by the connector assembly 64.

Figure 13:
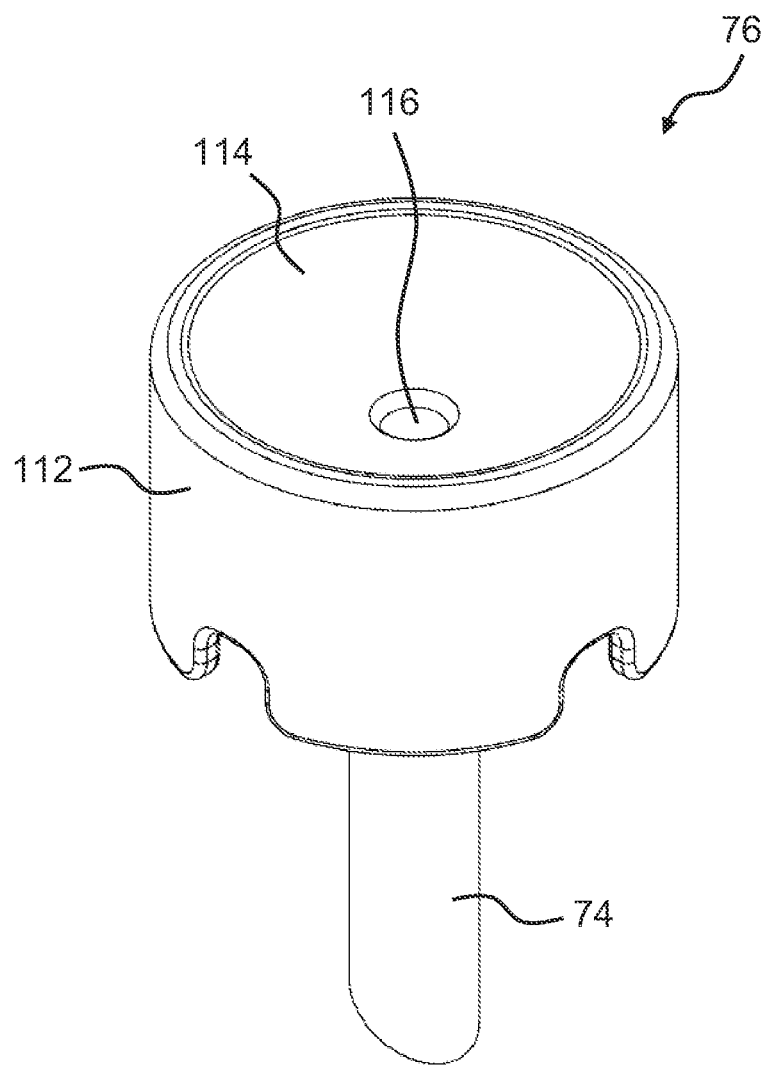
FIG. 13 is an isometric view of a funnel of the apparatus.
Figure 14:
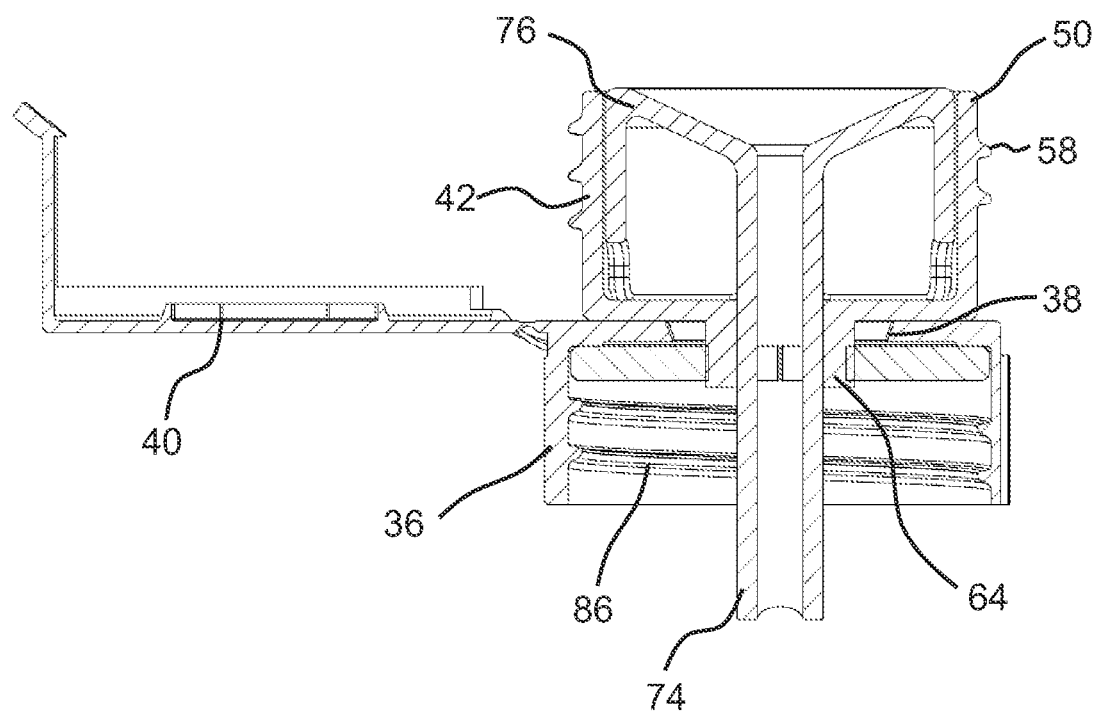
FIG. 14 is a cross sectional side elevation view of the funnel deployed in the adapter and cap.

As depicted in FIGS. 13, 14 and 15(a), a funnel 76 is insertable into the cylindrical body 50 of the adapter 42 for connecting the adapter 42 to a fluid outlet coupling port 44 of a further fluid sampling device 46. The funnel 76 comprises a fluid outlet tube 74 for receiving fluid from a fluid outlet 78 of the fluid outlet coupling port 44. The cap 36 and adapter 42 are mutually dimensioned such that the fluid outlet tube 74 extends through the aperture 38 of the cap 36 and protrudes through the perforations 70 into the storage region 68 when the adapter 42 is connected to the fluid outlet coupling port 44 and the cap 36 is connected to the adapter 42 by the connector assembly 64.

More particularly, in the example depicted the storage container 32 comprises a bottle of the type that is commonly used to collect and store oil samples. The adapter 42 is designed such that it is directly connectable to the fluid outlet coupling port 44 of a hand-operated vacuum pump 80 of the type shown in FIGS. 15(b) and 15(c). When the funnel 76 is placed inside the adapter 42 (as illustrated in FIG. 14) the adapter 42 is connectable to the fluid outlet coupling port 44 of an integrated fluid outlet device of the type shown in FIG. 15(a), as commonly provided on some mining vehicles and machinery.

Referring to FIGS. 3 to 6, the cap 36 may comprise a generally cylindrical hollow body with the aperture 38 extending vertically through the cap 36 between the uppermost and lowermost surfaces of the cap 36. The aperture 38 may comprise a generally circular central portion with a pair of rectangular portions 82 outwardly extending from opposed sides of the central portion. An outer cylindrical sidewall of the cap 36 may comprise a series of ribs, channels of similar textured surface features 84 that enable the cap 36 to be gripped effectively in use. The inner cylindrical sidewall of the cap 36 may comprise an internal screw thread 86 that is adapted to engage with a complementary screw thread provided on the neck of the bottle 32. In other examples, the cap 36 may be non-releasably attached to the bottle 32. For example, the cap 36 may be bonded to the bottle 32 using adhesive or the cap 36 may be integral with the bottle 32.

The lid 40 of the cap 36 is operatively configured to seal the aperture 38 releasably. The lid 40 may be hingedly connected to the cap 36 to provide a flip top mechanism that enables the lid 40 to be opened and closed as required. The lid 40 may comprise a fastener 88 that secures the lid 40 releasably to the cap 36 when the lid 40 is flipped into its closed position. The fastener 88 may comprise an elongate latch member provided with a hook 90 at one end that clips underneath a lowermost edge of the cap 36 when the lid 40 is closed. The outer sidewall of the cap 36 may comprise a vertically-aligned channel 92 formed therein. The channel 92 receives the latch member 88 such that the latch member 88 is aligned flush with the sidewall when the lid 40 is fastened down.

The lid 40 may also comprise an inwardly disposed skirt 94 projecting downwardly from a lowermost surface of the lid 40. The skirt 94 assists the lid 40 to seal the aperture 38 when the lid 40 is flipped down. The skirt 94 and aperture 38 are shaped complementary to one another such that the skirt 94 enters the aperture 38 and bears against an innermost peripheral wall 96 of the aperture 38 when the lid 40 is pressed down onto the cap 36. The innermost peripheral wall 96 may be tapered at an angle such that the surface area of the aperture 38 reduces in size towards its lowermost end. The skirt 94 may also be similarly inwardly tapered towards its lowermost end so that the skirt 94 bears against the tapered wall 96 of the aperture 38 when the lid is closed down. In this arrangement, it will be understood that the skirt 94 and wall 96 engage each other at a diagonal angle relative to the surface 39 of the cap 36. In the example depicted, the skirt 94 generally conforms to the shape of the aperture 38. However, in other examples the skirt 94 may have other shapes. For example, the skirt 94 and aperture 38 may each be circular. In another example, the aperture 38 may be shaped as depicted in FIG. 3 but the skirt 94 may be circular and be received into a circular channel (not shown) formed in the surface 39 of the lid 40 around the aperture 38.

Figure 3:
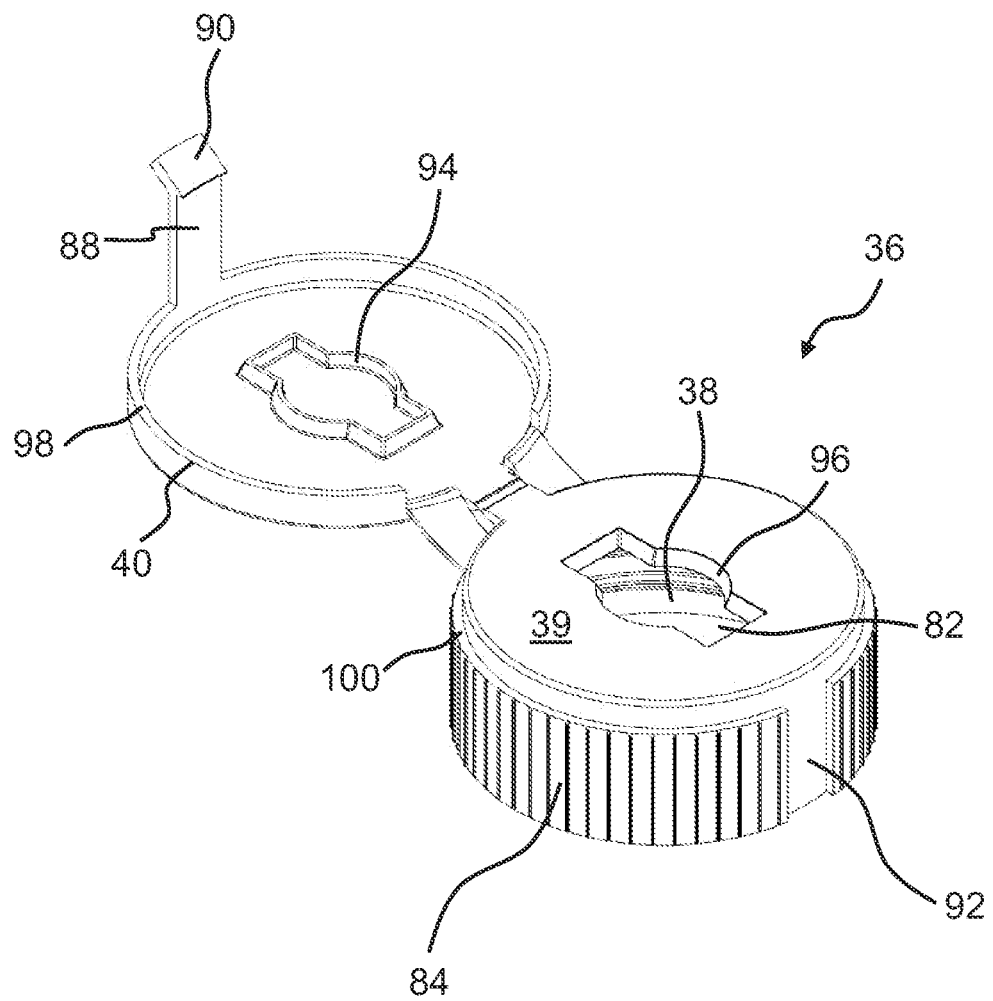
FIG. 3 is an isometric view of a cap of the apparatus.
Figure 4:
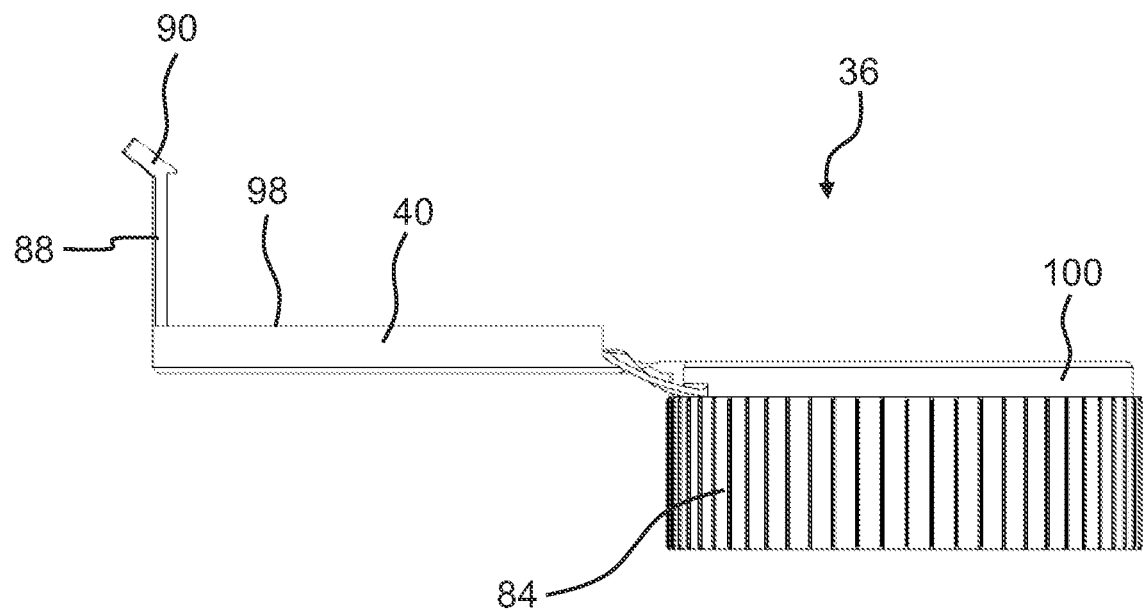
FIG. 4 is a side elevation view of the cap.
Figure 5:
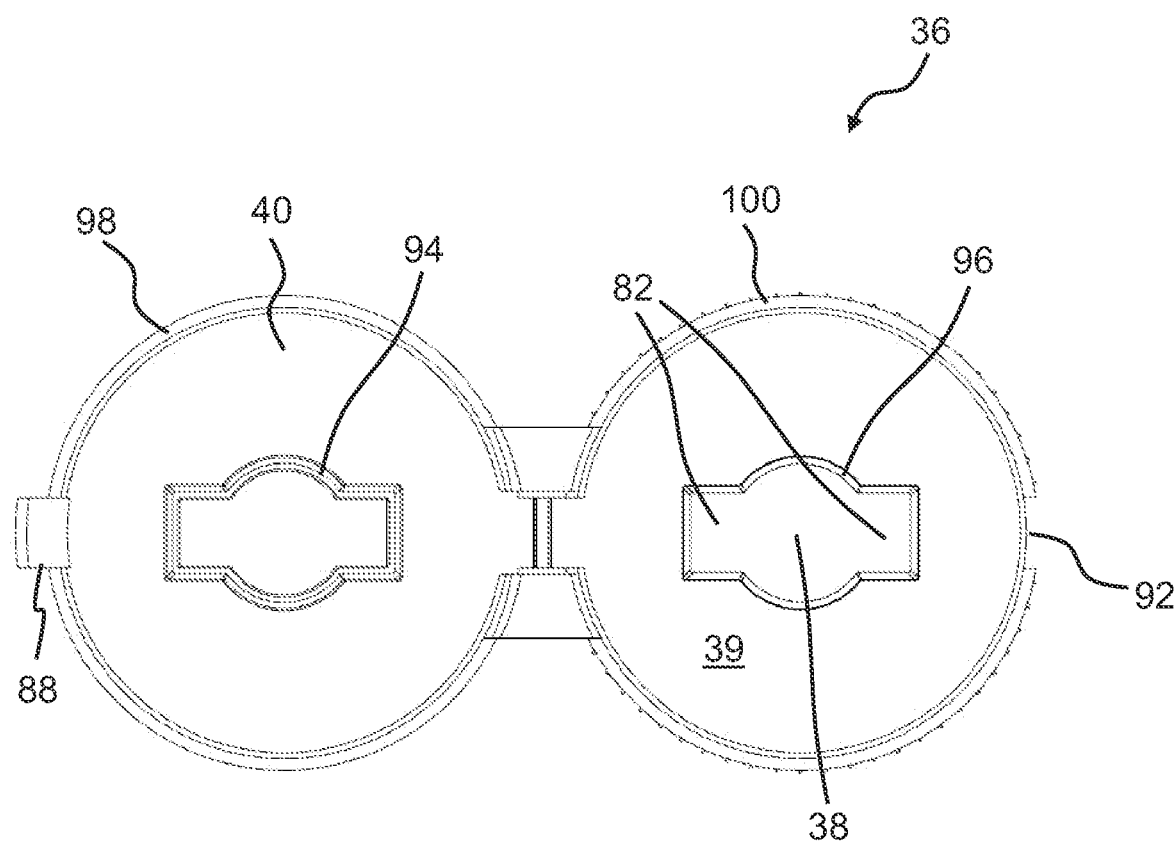
FIG. 5 is a plan view of the cap.

As best shown in FIG. 3, the lid 40 may also comprise a further downwardly projecting skirt 98 that is generally circular and extends around the outer circumference of the lid 40. When the lid 40 is flipped down, the skirt 98 engages around the uppermost surface 39 of the cap 36 and bears downwardly against the uppermost annular surface of a cylindrical collar 100 formed around the cap 36. The mutual engagements between the skirt 94 and the tapered aperture wall 96 and between the skirt 98 and the collar 100 further ensure that an airtight seal is achieved between the lid 40 and aperture 38 when the lid 40 is closed.

Figure 6:
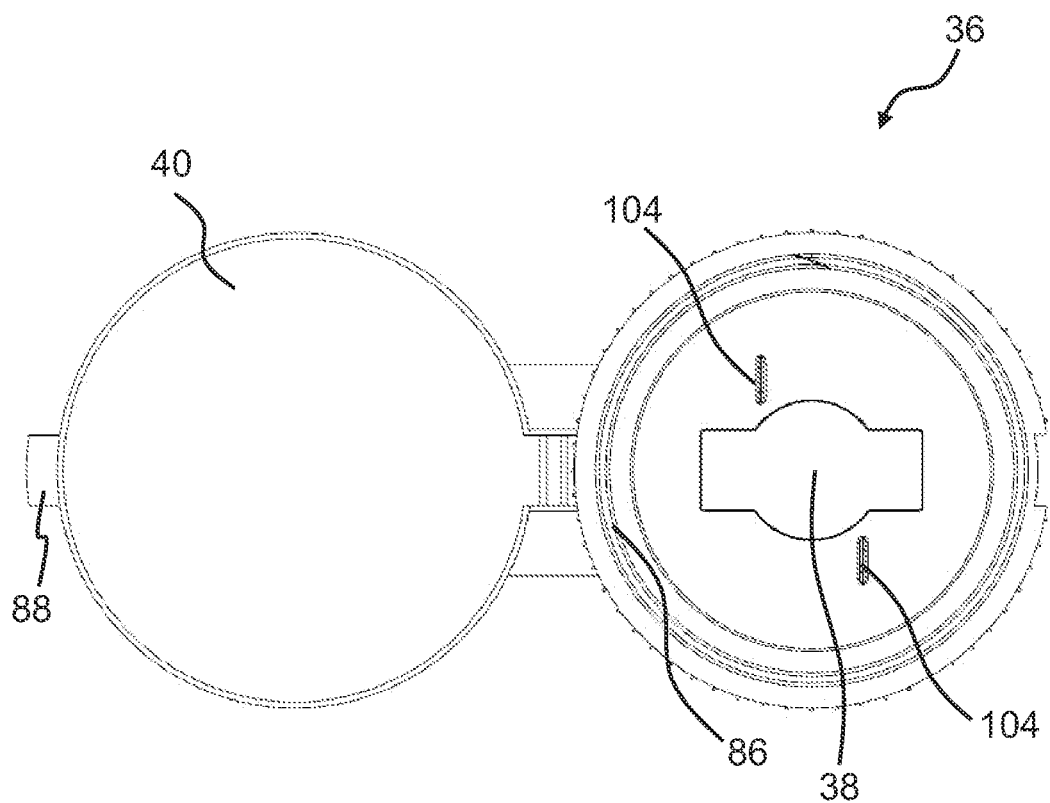
FIG. 6 is a bottom view of the cap.
Figure 7:
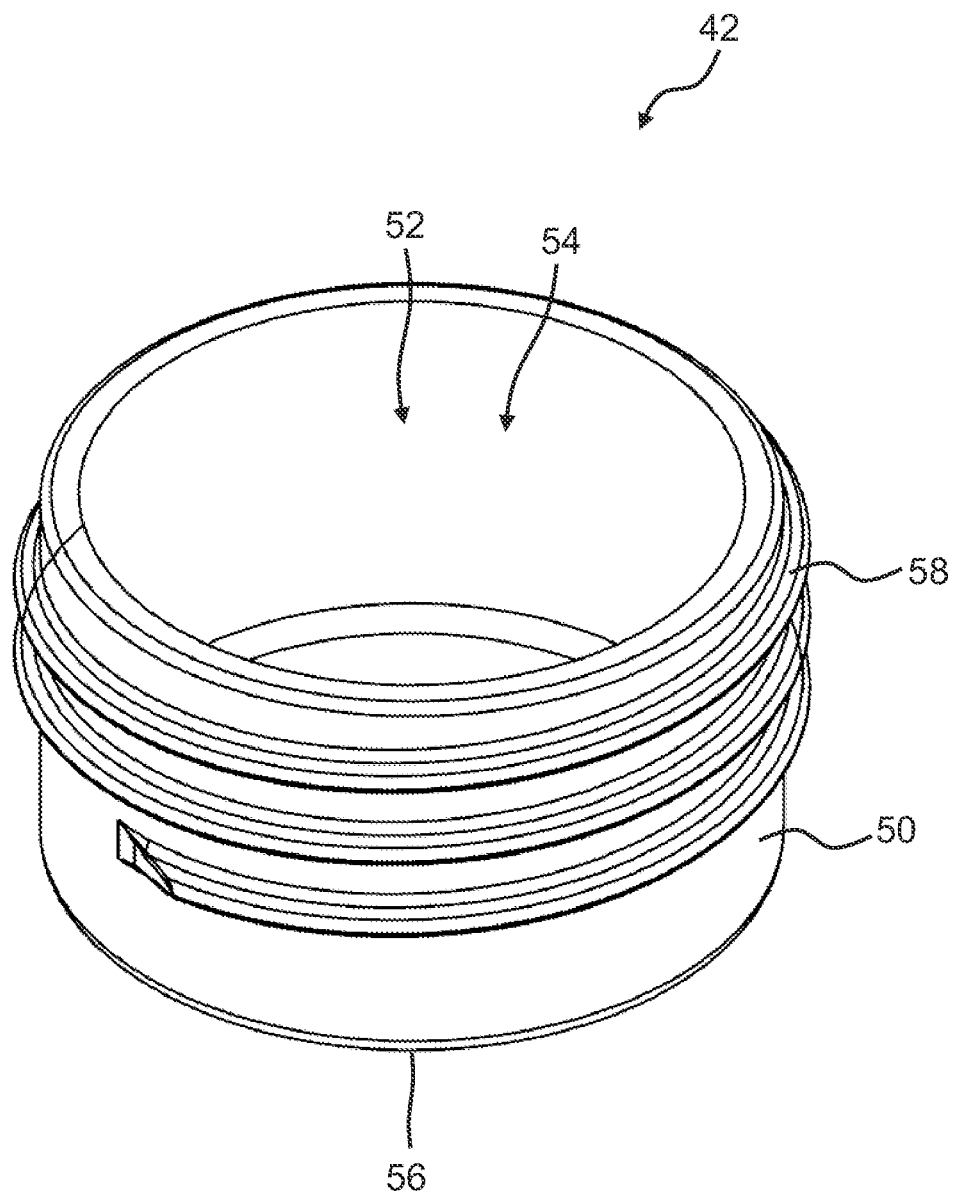
FIG. 7 is an isometric view of an adapter of the apparatus.
Figure 8:
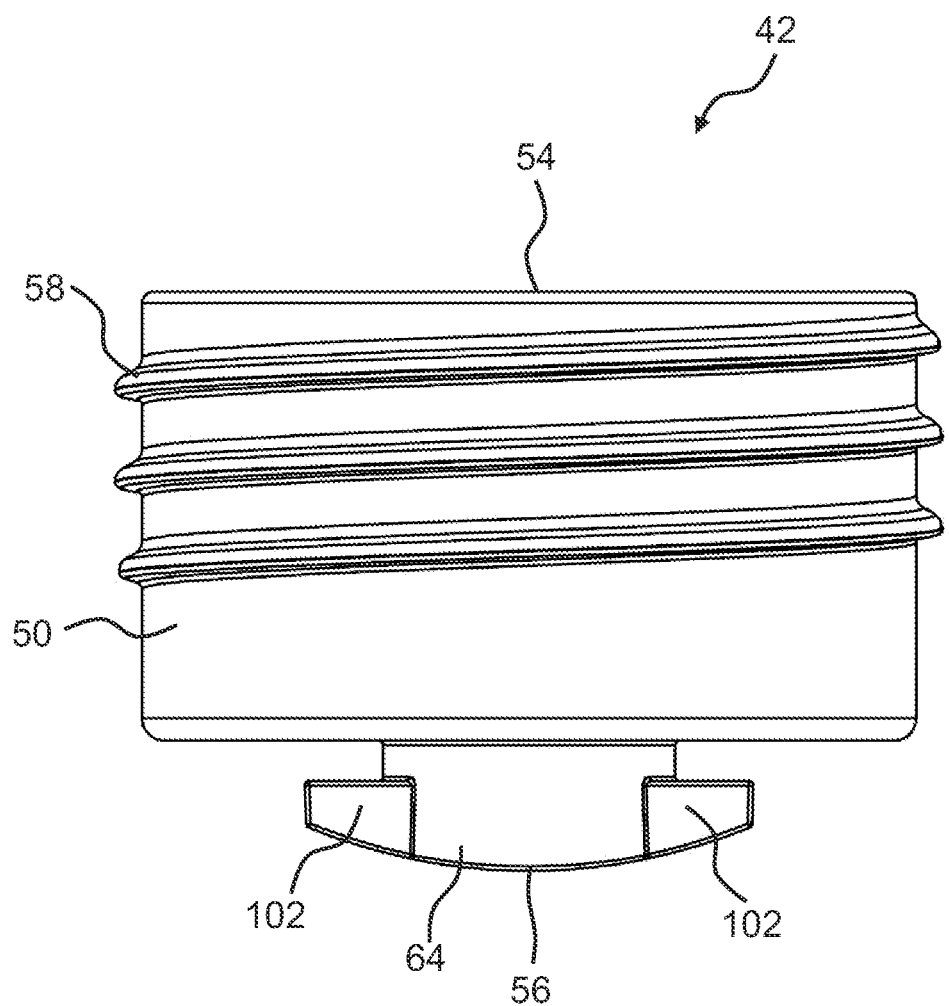
FIG. 8 is a side elevation view of the adapter.

Referring to FIGS. 7 to 10, the connector assembly 64 may be configured such that the adapter 42 and cap 36 connect together releasably via a twist lock mechanism. For example, the connector assembly 64 may comprise a boss that extends downwardly from a lowermost end of the adapter 42. The boss 64 may be dimensioned such that it protrudes through the aperture 38 of the cap 36 when the adapter 42 is pushed downwardly onto the cap 36. The boss 64 may comprise a pair of outwardly protruding locking members 102 that engage with an underside of the cap 36 when the adapter 42 is then twisted relative to the cap 36. As best shown in FIG. 6, the cap 36 may also comprise a pair of lugs 104 protruding downwardly from its underside. The locking members 102 of the adapter 42 may bear against the lugs 104 when the adapter 42 has been twisted relative to the cap 36 by a maximum extent. In other examples, instead of a twist lock mechanism the connector assembly 64 may comprise a push-fit or snap-fit locking mechanism that allows the cap 36 and adapter 42 to be releasably connected together rapidly and securely in use.

Figure 9:
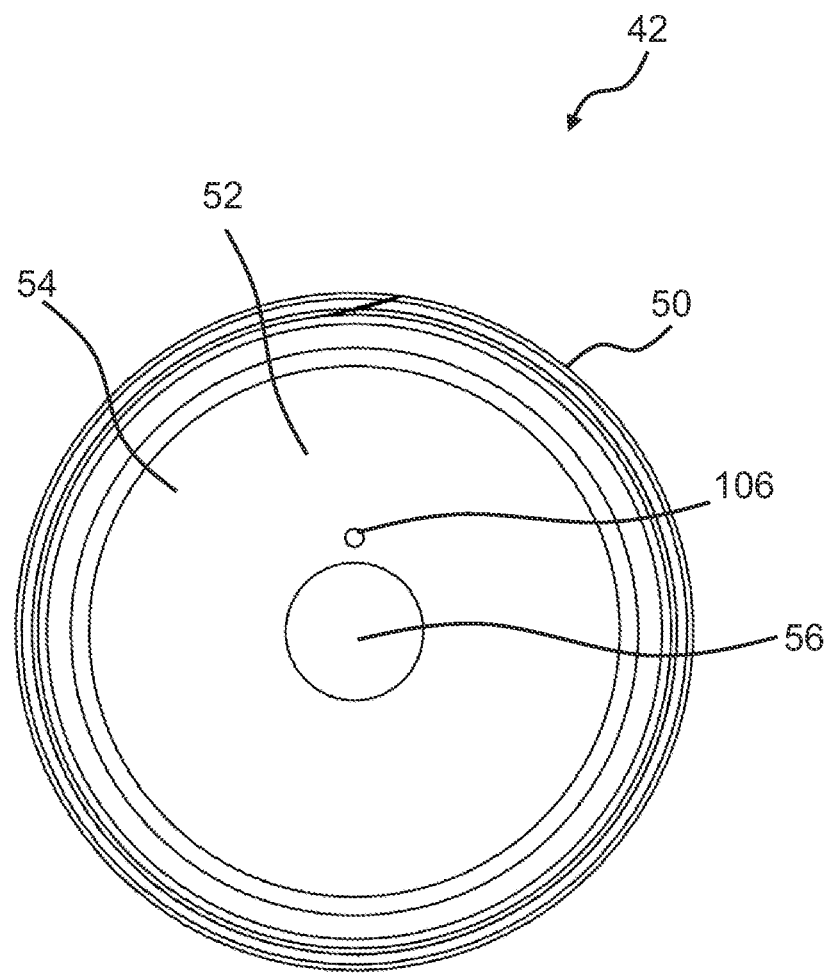
FIG. 9 is a plan view of the adapter.
Figure 10:
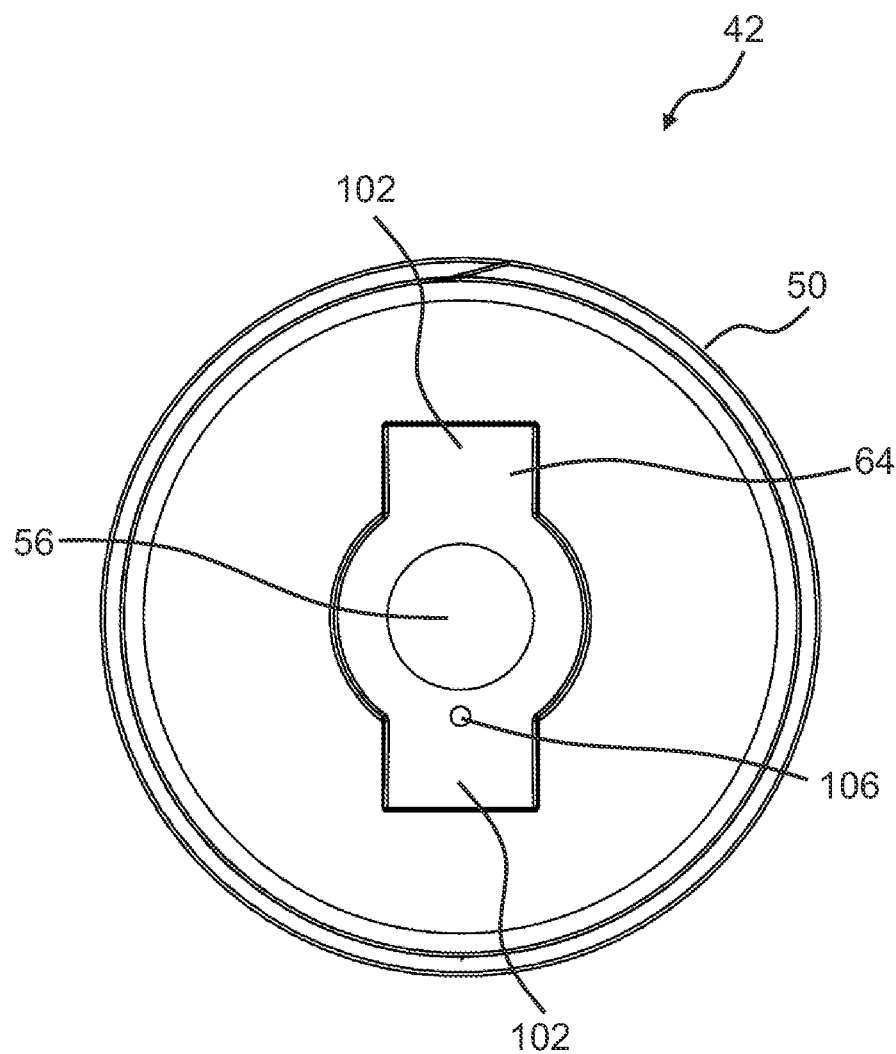
FIG. 10 is a bottom view of the adapter.

The cylindrical body 50 of the adapter 42 may be hollow and comprise an internal lumen 52 extending between the inlet aperture 54 and the outlet aperture 56 of the body 50. The lumen 52 may extend through the boss 64 such that the outlet aperture 56 is provided at the lowermost end of the boss 64. The adapter 42 may also comprise at least one air vent that allows air to escape from the storage container 32 when fluid flows therein from the fluid sampling device 46. As shown in FIGS. 9 and 10, the vent may comprise a small aperture 106 that extends vertically through the boss 64 and opens out into the lumen 52. In other examples, the vent may be formed directly into the cap 36 and may comprise a one-way valve assembly that only permits air to travel out of the storage container 32 through the vent. The external screw thread 58 on the cylindrical body 50 allows the adapter 42 to be screwed into internally threaded coupling ports 44 of fluid sampling devices. In other examples, the body 50 may comprise one or more clips or similar fasteners to enable the adapter 42 to be secured to coupling ports of devices not featuring internal screw threads.

Figure 2:
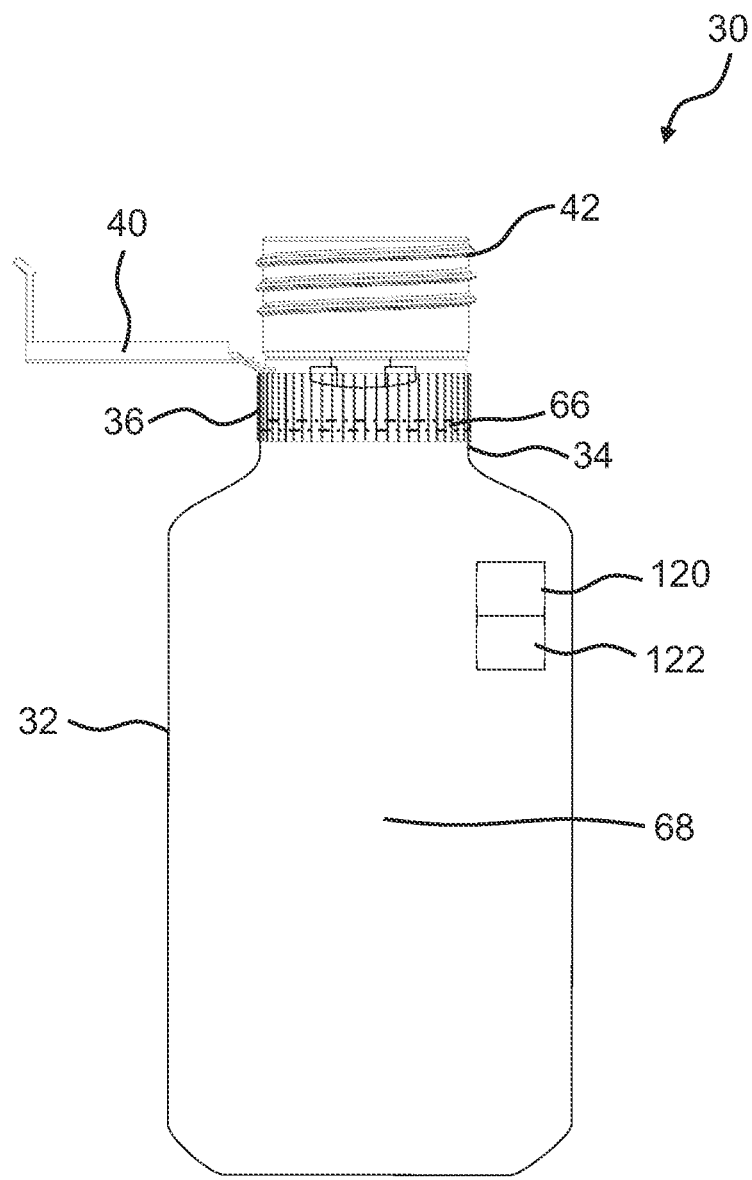
FIG. 2 is a side elevation view of an apparatus for collecting and storing fluid samples from vehicles and machinery according to an example embodiment of the invention.
Figure 11:
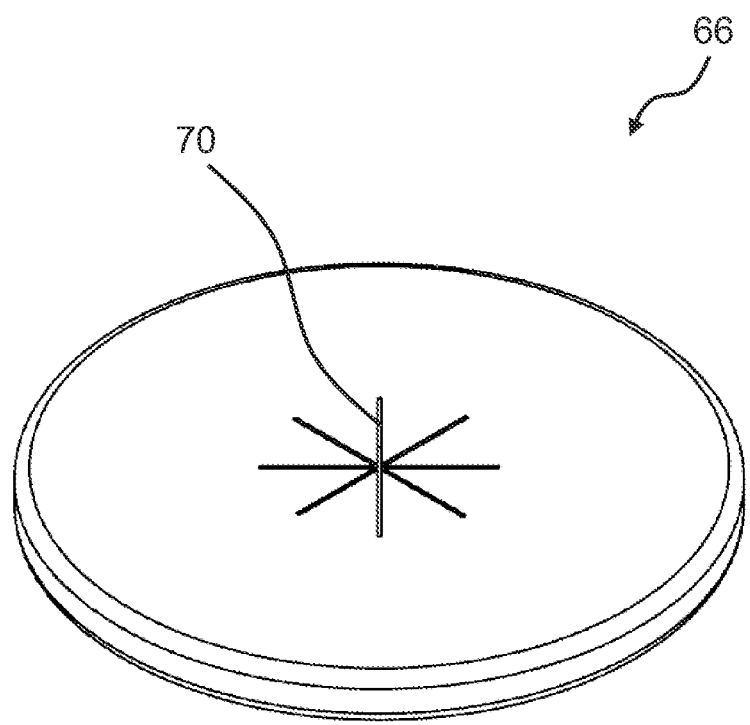
FIG. 11 is an isometric view of a penetrable diaphragm of the apparatus.
Figure 12:
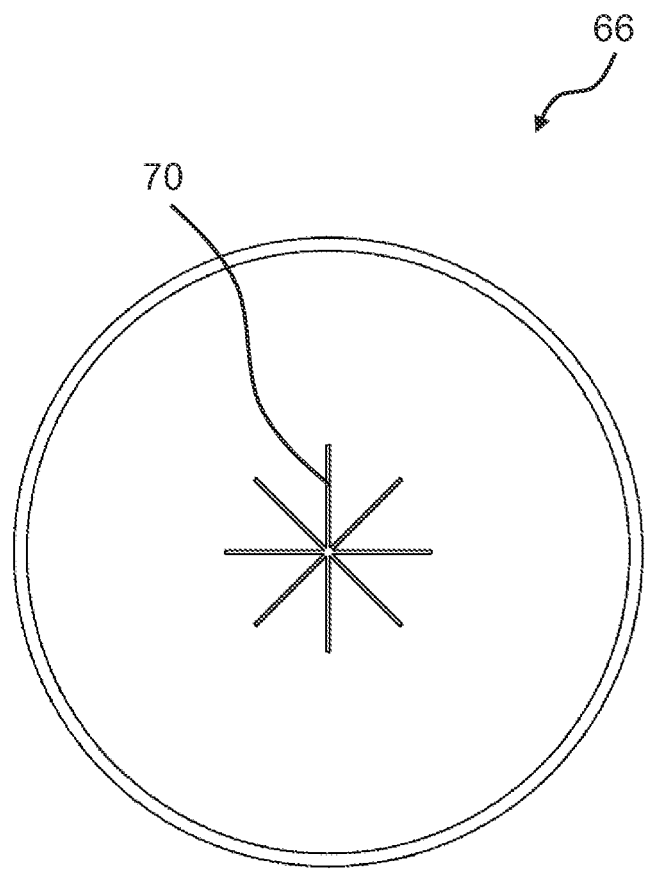
FIG. 12 is a plan view of the penetrable diaphragm.

The diaphragm 66 provides an airtight seal over the storage region 68 of the bottle 32. In use, the diaphragm 66 is penetrated by the fluid outlet tube 72 of the vacuum pump 80, or by the fluid outlet tube 74 of the funnel 76, when the apparatus 10 is connected to the relevant fluid sampling device. Referring to FIGS. 11 and 12, the diaphragm 66 may comprise a circular membrane that is made from an elastically deformable material, such as plastic or rubber, that has one or more perforations 70 formed therein. In the example provided, the diaphragm 66 comprises a plurality of perforations 70 in a star arrangement to form a plurality of inwardly projecting triangular flaps that are elastically bendable. As shown in FIG. 2, the diaphragm 66 may be disposed inside the cap 36 spaced apart from the uppermost surface 39 of the cap 36. The diaphragm 66 may be bonded to the inner sidewall of the cap 36, for example using adhesive, or it may be held in position by an inwardly protruding annular ridge (not shown) extending around the inner sidewall. In another example, the diaphragm 66 may be connected to an inside surface of the bottle 32 below the cap 36. In another example, the penetrable diaphragm 66 may comprise a plurality of elastically flexible flaps that project inwardly from the side wall 96 of the aperture 38 of the cap 36. In the latter example, in lieu of the boss 64 and locking members 102 the adapter 42 may comprise a mechanism that is connectable to an engagement member provided on or above the uppermost surface 39 of the cap 36.

In use, the bottle 32 is provided initially with its cap 36 screwed on and with the lid 40 closed against the cap 36 sealing the aperture 38. When a fluid sample needs to be taken from a vehicle 48, the adapter 42 may firstly be connected to the vacuum pump 80 by screwing the adapter 42 into the fluid coupling port 44 of the pump 80. An inlet end of the pump's sampling tube 108 may then be inserted into a compartment of the vehicle 48 that the sample is to be taken from. The lid 40 of the cap 36 may then be flipped open to expose the aperture 38. The bottle 32 may then be offered up to the adapter 42 so that the boss 64 protrudes through the aperture 38. The bottle 32 may then be twisted relative to the adapter 42 causing the locking members 102 to engage with the underside of the cap 36 thus connecting the cap 36 and adapter 42 together. The locking members 102 bear against the lugs 104 when the cap 36 has been twisted relative to the adapter 42 by a maximum extent. When the bottle 32 is connected to the adapter 42, the fluid outlet tube 72 of the pump 80 protrudes through the perforations 70 of the diaphragm 66 into the storage region 68 of the bottle 32.

The pump 80 may then be operated to extract the required quantity of fluid from the relevant compartment of the vehicle 48 into the bottle 32. Once the fluid sample has been taken, the bottle 32 may be twisted relative to the adapter 42 in the opposite direction and pulled in a downwards direction so that the bottle 32 disengages from the adapter 42. The lid 40 may then be flipped downwards onto the cap 36 to seal the aperture 38.

The apparatus 30 advantageously enables a fluid sample to be obtained without any contamination occurring that would materially affect the results of laboratory tests subsequently carried out on the sample. In particular, the sealable cap 36, penetrable diaphragm 66 and adapter 42 provide for sealed fluid communication between the fluid sampling device 46 and the bottle 32. The apparatus 30 is advantageously robust in construction, easy to use and is particularly effective at reducing the risk of contamination in windy and dusty environments.

Referring to FIG. 13, a funnel device 76 is shown that may also be used in embodiments of the invention. The funnel 76 is used as an interface for connecting the cap 36 and adapter 42 to fluid sampling devices that do not feature fluid outlet tubes (sampling tubes). For example, as illustrated in FIG. 15(a) some mining vehicles comprise one or more integrated fluid sampling outlets 110 that are provided at locations on the vehicle that are convenient to access. Each outlet 110 may incorporate its own pump (electric or manually operated) which when operated causes a vehicle compartment fluid, such as oil, to be pumped out of an outlet 78 provided in the aperture 62 of a coupling port 44 of the outlet 110.

The funnel 76 may comprise a generally cylindrical body 112 having a conical-shaped inlet 114 at its topmost end. A fluid outlet tube 74 may extend downwardly from the body 112. An aperture 116 at a base end of the inlet 114 provides a fluid exit in fluid communication with the tube 74. The outlet 78 of the sampling device 110 may also be conical-shaped which is received by the inlet 114 to form a sealed connection therewith. In use, the funnel 76 is placed inside the lumen 52 of the adapter 42 and the adapter 42 is then screwed into the coupling port 44 of the sampling outlet 110. The opened cap 36 of the bottle 32 is then connected to the adapter 42. The tube 74 of the funnel 76 protrudes through the perforations 70 of the penetrable diaphragm 66 into the storage region of the bottle 32. The pump of the sampling outlet 110 may then be switched on causing vehicle compartment fluid to flow from the outlet 110 into the bottle 32. In the example depicted, the funnel 76 is a separate component that is removably insertable into the lumen 52 of the adapter 42. In other examples, the funnel 76 may be integral with the adapter 42 and the conical-shaped inlet 114 and outlet tube 74 of the funnel 76 may provide the lumen 52 of the adapter 42.

In further examples, as illustrated in FIG. 2 the apparatus 30 may also comprise a digital storage device 120 for recording data about a fluid sample contained in the bottle 32. A wireless transceiver 122 may also be provided for connecting the storage device 120 to a peripheral device that writes/reads such data to/from the storage device 120. For example, the storage device 120 and transceiver 122 may comprise a radio-frequency identification (RFID) tag attached to or embedded in a sticker or label affixed to a side of the bottle 32. In other examples, the RFID tag may be embedded into the cap 36. The RFID tag may be passive or active and hold electronically stored data relating to the fluid sample. The data may comprise, for example, the time and date that the sample was obtained, the fluid type and information about the vehicle or equipment that the sample was extracted from.

The peripheral device may be a smartphone or similar mobile digital device that executes software that interacts with the RFID tag. In other examples, the peripheral device may be attached to the vehicle or equipment that the fluid sample is extracted from and may write data to the RFID tag when the sample is taken. For example, the peripheral device may be attached to a fluid outlet on the vehicle or equipment and write data to the RFID tag when the apparatus 30 is placed near to the fluid outlet when the sample is being taken. The peripheral device may also be communicatively coupled to a remote server and be configured to transmit data relating to fluid samples to the server for storage and subsequent analysis. The RFID tag provides for traceability of fluid samples and enables samples to be accurately recorded and managed.

In addition to reading/writing information from/to the RFID tag or relevant digital storage device 120 of the apparatus 30, the peripheral device may also receive information from one or more field devices that are capable of measuring physical characteristics and conditions relating to the fluid sample and/or the environment in which the sample was obtained. For example, the peripheral device may receive information from an hour meter, temperature sensor or humidity sensor used by the person who is collecting the fluid sample. The peripheral device may associate the information received from the field device(s) with the information received from the digital storage device 120 and send the combined information to the server. For example, the peripheral device may be connected to an oil temperature sensor that is located in the engine compartment that an oil sample is taken from. The measured oil temperature may be associated with the relevant fluid sample data retrieved from the RFID tag and stored on the server. In other examples, the peripheral device may be remotely connectable to one or more mobile field devices held by the person taking the sample that are used to measure environmental conditions when the sample was obtained.

Figure 17A:
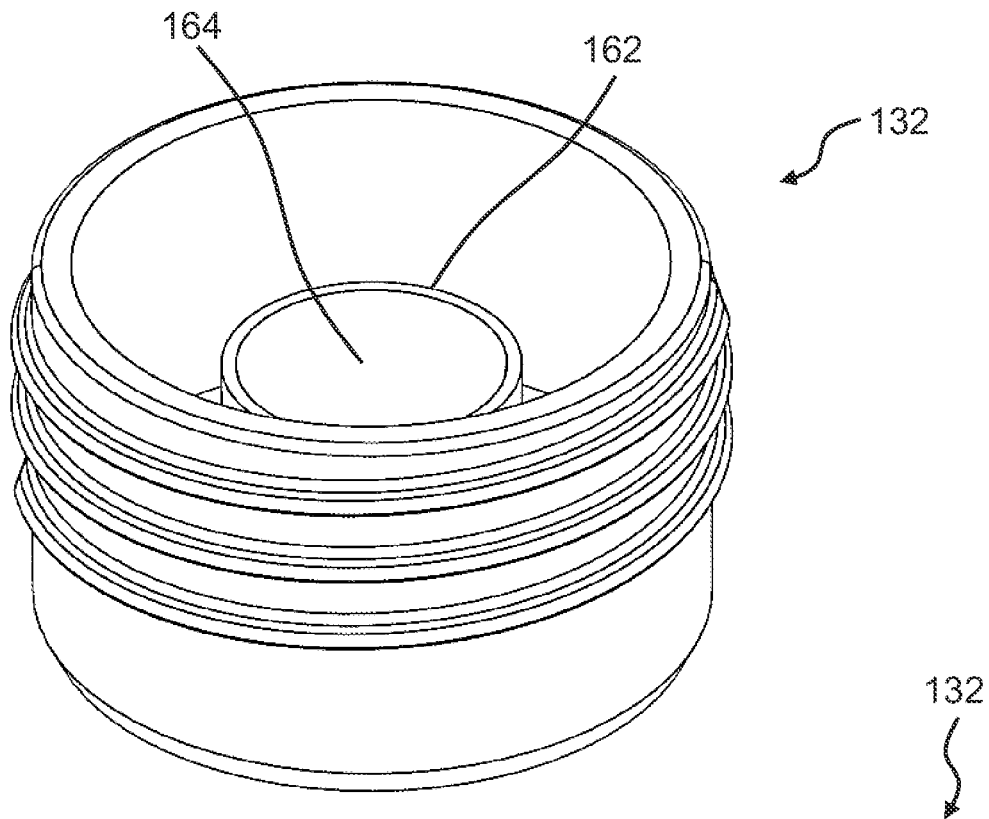
FIG. 17(a) is an isometric view of an adapter included in the apparatus according to the further embodiment.
Figure 17B:
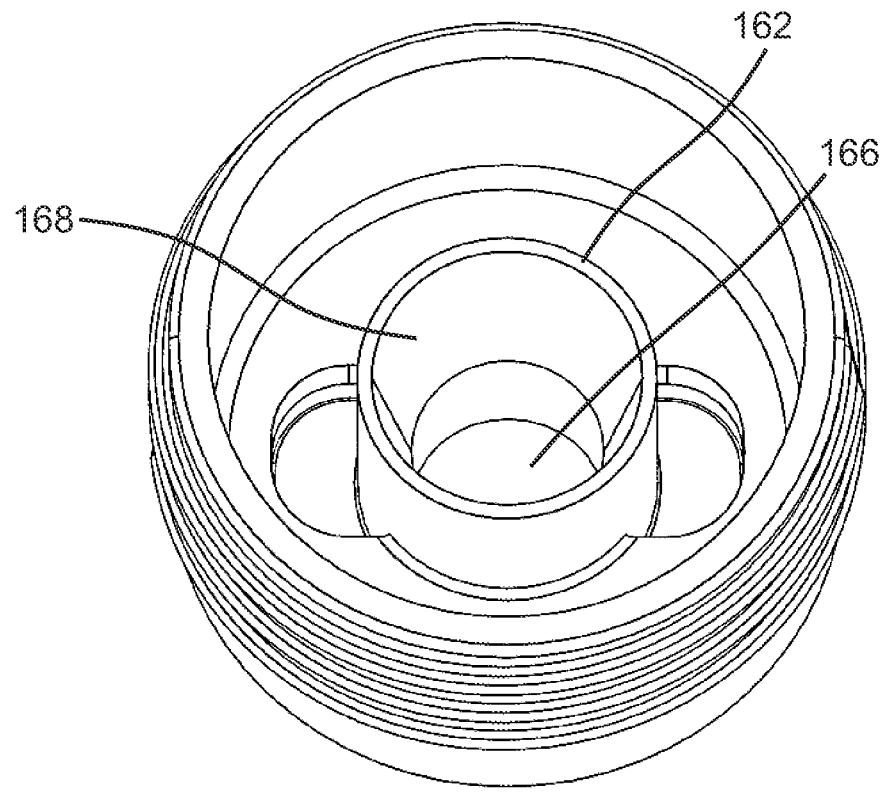
FIG. 17(b) is a further isometric view of the adapter of FIG. 17(a)
Figure 18A:
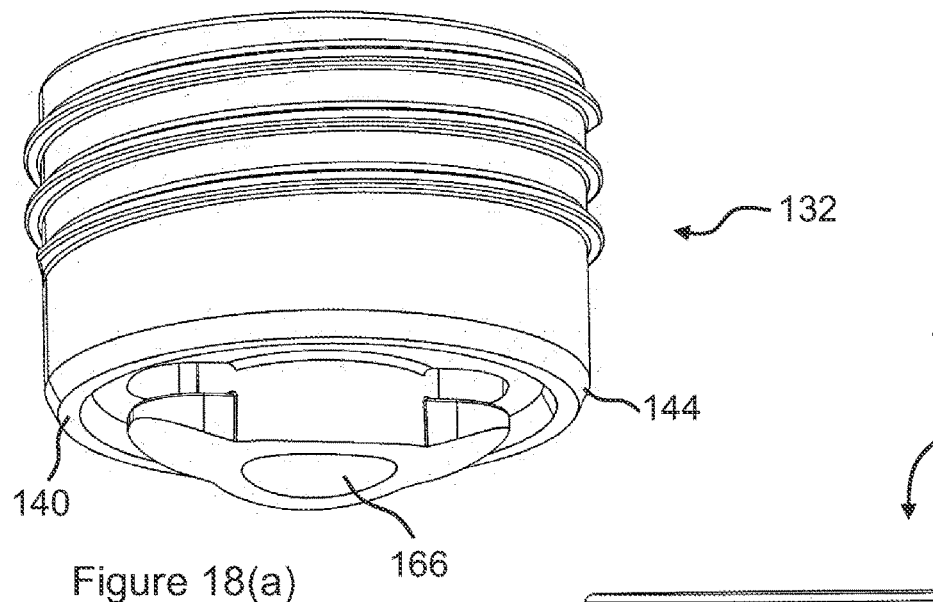
FIG. 18(a) is a further isometric view of the adapter of FIG. 17(a)
Figure 18B:
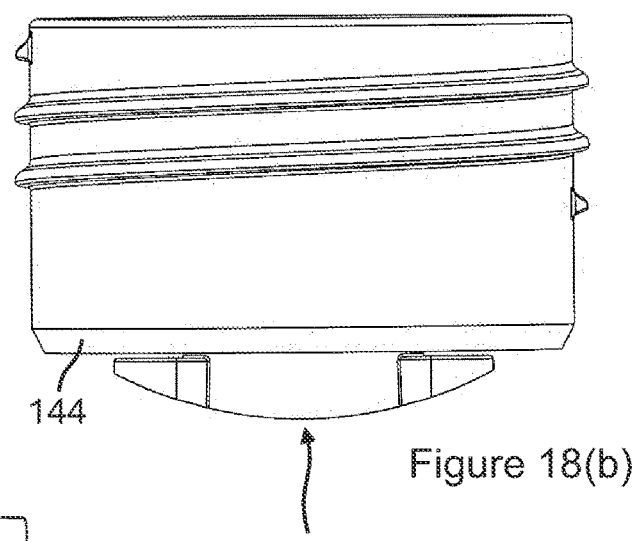
FIG. 18(b) is a side elevation view of the adapter of FIG. 17(a)
Figure 18C:
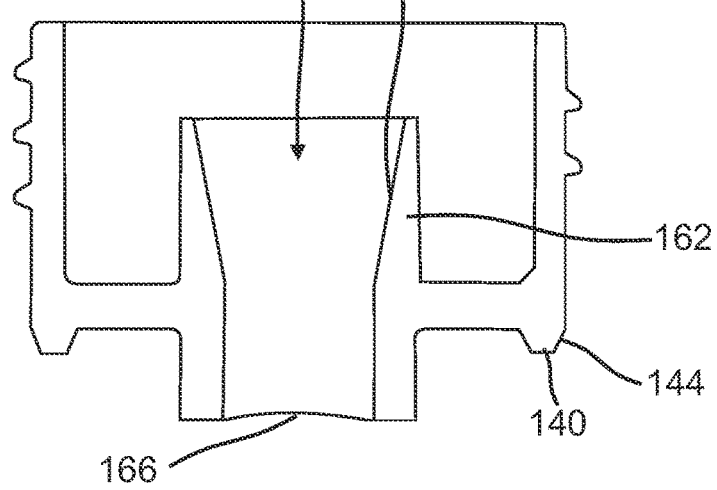
FIG. 18(c) is a cross sectional side elevation view of the adapter of FIG. 17(a).

Referring now to FIGS. 16 to 18, further examples of a cap 130 and an adapter 132 are shown that may be included in an apparatus for collecting and storing fluid samples from vehicles and machinery according to a further example embodiment of the invention. The cap 130 and adapter 132 are similar in structure and function to the cap 36 and adapter 42 depicted in the preceding Figures. However, the cap 130 also comprises an annular channel 134 provided in the uppermost surface 136 of the cap 130. The channel 134 extends around the aperture 138 of the cap 130 and is disposed inward from the outer circumference of the cap 130 by a short distance. The adapter 132 comprises an annular ridge 140 protruding downwardly from the lowermost circular end of its cylindrical body. The ridge 140 is adapted to engage into the channel 134 in the cap 130 when the adapter 132 and cap 130 are connected together. A radially outermost wall 142 of the channel 134 and radially outermost wall 144 of the ridge 140 may be mutually tapered such that they engage each other diagonally relative to the surface 136 of the cap 130. The ridge 140 and channel 142 configuration ensures that an airtight seal is achieved between the adapter 132 and the cap 130 when they are connected together.

The lid 146 of the cap 130 may also comprise an annular ridge 148 that protrudes downwardly from an underside of the lid 146. The ridge 148 is adapted to engage into the annular channel 134 when the lid 146 is closed. A radially outermost wall 150 of the ridge 148 is also mutually tapered with the outermost wall 142 of the channel 134 so that the walls engage each other diagonally relative to the surface 136 of the cap 130.

The cap 130 also comprises a ridge 152 that upwardly extends from the surface 136 of the cap 130 around a perimeter of the aperture 138. The lid 146 comprises a first skirt 154 protruding downwardly from an underside of the lid 146 that bears against an innermost wall of the ridge 152 when the lid 146 seals the aperture 138. The lid 146 also comprises a second skirt 156 protruding downwardly from the lid's underside that is outwardly spaced from the first skirt 154. The second skirt 156 is dimensioned to engage with a radially outermost surface of the ridge 152 when the lid 146 seals the aperture 138 of the cap 130. In this configuration, the two skirts 154, 156 straddle the ridge 152 when the lid 146 is closed down to further ensure that an airtight seal is achieved between the lid 146 and the cap 130. In the example depicted, the ridge 152 and skirts 154, 156 generally conform to the shape of the aperture 138. However, these components may have other shapes. For example, the ridge 152 and skirts 154, 156 may be circular and extend around the aperture 138 at a fixed radius. As best shown in FIGS. 16(*c*) and 16(*d*), the cap 130 also comprises an annular projection 158 extending downwardly from the underside of the cap 130. A radially outermost surface 160 of the annular projection 158 may be tapered such that it bears against an innermost edge of an annular lip of the mouth 34 of the bottle 32 when the cap 130 is attached thereto.

The adapter 132 is configured to engage with fluid outlet coupling ports 44 of hand-operated vacuum pumps 80 of the type shown in FIGS. 15(*b*) and 15(*c*). Rather than being completely hollow, the cylindrical body of the adapter 132 comprises a receptor 162 disposed centrally within the body. An internal lumen 164 extends vertically through the receptor 162 which is in fluid communication with the outlet aperture 166 at the lowermost end of the adapter's body. The internal wall 168 of the lumen 164 may be conical shaped so as to receive and guide the outlet tube 72 extending from the fluid outlet coupling port 44 through the lumen 164 and into the bottle 32 in use.

For the purpose of this specification, the word "comprising" means "including but not limited to", and the word "comprises" has a corresponding meaning.

The above embodiments have been described by way of example only and modifications are possible within the scope of the claims that follow.

The invention claimed is:

1. An apparatus for collecting and storing fluid samples from vehicles and machinery, the apparatus comprising:
a storage container having a fluid inlet;
a cap for sealing the fluid inlet, wherein the cap comprises an aperture in a surface of the cap and a lid for releasably sealing the aperture;
an adapter for releasably connecting the cap to a fluid outlet coupling port of a fluid sampling device, the fluid sampling device being configured to collect a fluid sample from a vehicle or machine, wherein the adapter comprises a body having an internal lumen extending longitudinally between inlet and outlet apertures of the body, wherein the inlet aperture of the body is configured to engage fluidly with the fluid outlet coupling port, and a connector assembly for fluidly connecting the outlet aperture of the body to the aperture in the cap, wherein the surface of the cap and a lowermost end of the body are mutually adapted to provide an airtight seal therebetween when the adapter and cap are connected together by the connector assembly;
a penetrable diaphragm disposed inside the cap or the storage container that provides an airtight seal over a storage region of the storage container below the penetrable diaphragm, wherein the penetrable diaphragm has one or more premade perforations therein, wherein the one or more premade perforations provide a plurality of elastically bendable flaps for receiving, through the penetrable diaphragm, a fluid outlet tube of the fluid sampling device to receive the fluid sample into the storage region;
an annular channel provided in the surface of the cap that extends around the aperture of the cap; and
an annular ridge that protrudes downwardly from an underside of the lid that is adapted to engage into the annular channel when the lid is closed,
wherein the cap and adapter are mutually dimensioned such that the fluid outlet tube extends through the aperture of the cap and protrudes through the flaps into the storage region when the adapter is connected to the fluid outlet coupling port and when the cap is connected to the adapter.

2. The apparatus according to claim 1, wherein the connector assembly comprises a twist lock mechanism.

3. The apparatus according to claim 2, wherein the twist lock mechanism comprises a boss downwardly extending from the body, the boss comprising one or more outwardly protruding locking members that engage an underside of the cap when the cap and adapter are twisted relative to each other.

4. The apparatus according to claim 3, wherein one or more lugs are provided on the underside of the cap, and wherein the locking members bear against the lugs when the cap and adapter are twisted relative to each other by a maximum extent.

5. The apparatus according to claim 1, wherein an annular channel is provided in the surface of the cap that extends around the aperture of the cap, and wherein an annular ridge protrudes downwardly from a lowermost end of the body of the adapter that is adapted to engage into the annular channel when the adapter and cap are connected together.

6. The apparatus according to claim 5, wherein a radially outermost wall of the annular channel and a radially outermost wall of the annular ridge are mutually tapered such that they engage each other diagonally relative to the surface of the cap.

7. The apparatus according to claim 1, wherein a radially outermost wall of the annular channel and a radially outermost wall of the annular ridge are mutually tapered such that they engage each other diagonally relative to the surface of the cap.

8. The apparatus according to claim 1, wherein a surface of the penetrable diaphragm has a plurality of the perforations.

9. The apparatus according to claim 1, wherein the cap comprises a screw thread that threadedly engages with a complimentary screw thread provided on the fluid inlet of the storage container.

10. The apparatus according to claim 1, wherein the cap comprises an annular projection extending downwardly from an underside of the cap, and wherein a radially outermost surface of the annular projection is tapered and adapted to bear against an annular lip of the fluid inlet of the storage container when the cap is attached thereto.

11. The apparatus according to claim 1, wherein the lid comprises a skirt protruding downwardly from an underside of the lid, wherein the skirt is dimensioned to bear against an innermost wall of the aperture of the cap when the lid seals the aperture.

12. The apparatus according to claim 11, wherein the skirt and innermost wall of the aperture are mutually tapered to engage each other diagonally relative to the surface of the cap when the lid seals the aperture of the cap.

13. The apparatus according to claim 11, wherein the cap comprises a peripheral ridge that upwardly extends from the surface of the cap around a perimeter of the aperture of the cap, and wherein the lid comprises a second skirt protruding downwardly from an underside of the lid, wherein the second skirt is dimensioned to engage with a radially outermost wall of the peripheral ridge when the lid seals the aperture of the cap.

14. The apparatus according to claim 1, wherein the apparatus comprises at least one air vent to allow air to escape from the storage container when fluid flows therein from the fluid sampling device.

15. The apparatus according to claim 1, wherein the apparatus comprises a digital storage device for recording data relating to a fluid sample contained in the storage container.

16. The apparatus according to claim 15, wherein the digital storage device is provided with a wireless transceiver for transferring and receiving data relating to the fluid sample to and from a peripheral device remote from the storage container.

17. The apparatus according to claim 16, wherein the digital storage device comprises an RFID.

18. The apparatus according to claim 15, wherein the digital storage device is attached to or embedded in a sticker or label affixed to the storage container.

* * * * *